US00PP37079P2

(12) United States Plant Patent
Lim

(10) Patent No.: US PP37,079 P2
(45) Date of Patent: Nov. 4, 2025

(54) CLIMBING ROSE PLANT NAMED 'ALTenglanda'

(50) Latin Name: *Rosa hybrida*
Varietal Denomination: ALTenglanda

(71) Applicant: Altman Specialty Plants llc, Vista, CA (US)

(72) Inventor: Peter Lim, Escondido, CA (US)

(73) Assignee: Altman Specialty Plants Inc, Vista, CA (US)

( * ) Notice: Subject to any disclaimer, the term of this patent is extended or adjusted under 35 U.S.C. 154(b) by 0 days.

(21) Appl. No.: 19/022,499

(22) Filed: Jan. 15, 2025

(51) Int. Cl.
*A01H 5/02* (2018.01)
*A01H 6/74* (2018.01)

(52) U.S. Cl.
USPC ..... Plt./112

(58) Field of Classification Search
USPC ..... Plt./146, 148, 105, 107, 113, 114, 112
CPC . A01H 5/02; A01H 5/00; A01H 6/749; A01H 6/74
See application file for complete search history.

(56) References Cited

U.S. PATENT DOCUMENTS

PP18,124 P2 * 10/2007 Maycen ..... A01H 5/02
Plt./308

OTHER PUBLICATIONS

American Rose Society, New Rose Introductions 2024, retrieved on Mar. 26, 2025 at https://rose.org/new-rose-introductions-2024/, 14 pp. (Year: 2025).*

Perwich, New roses debut: How many of these beauties will you plant in 2025, retrieved on Mar. 26, 2025 at https://www.sandiegouniontribune.com/2024/12/07/new-roses-debut-how-many-of-these-beauties-will-you-plant-in-2025/, 13 pp. (Year: 2024).*

* cited by examiner

*Primary Examiner* — June Hwu
(74) *Attorney, Agent, or Firm* — Cassandra Bright

(57) ABSTRACT

A new and distinct cultivar of Rose plant named 'ALTenglanda' is disclosed, characterized by distinctive fully double flowers rich apricot flowers with an average of 50 to 60 petals. The new cultivar is a vigorous upright shrub rose with continuous repeat flowering after the second year of planting. Plants have dark, foliage resistant to black spot and powdery mildew disease. The new variety is normally produced as an outdoor garden or container plant.

1 Drawing Sheet

Latin name of the genus and species: *Rosa hybrida.*
Variety denomination: 'ALTenglanda'.

BACKGROUND OF THE INVENTION

The new *Rosa* cultivar is a product of a planned breeding program conducted by the inventor, Peter Lim. The objective of the breeding program was to produce vigorous new garden rose varieties for ornamental commercial applications. The cross resulting in this new variety was made in Vista, California in May of 2013.

The seed parent is an unnamed, unpatented proprietary variety. The pollen parent is the unpatented variety *Rosa* 'Westerland'. The new variety was selected in June of 2014 by the inventor in a group of seedlings resulting from the 2013 crossing, in a nursery in Vista, California.

Asexual reproduction of the new cultivar has been performed by vegetative cuttings. This was first performed at a research greenhouse in Vista, California in June of 2014 and has shown that the unique features of this cultivar are stable and reproduced true to type in more than 5 successive generations.

SUMMARY OF THE INVENTION

The cultivar 'ALTenglanda' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ALTenglanda' These characteristics in combination distinguish 'ALTenglanda' as a new and distinct *Rosa* cultivar:

1. Vigorous upright climbing rose.
2. Double flower with an average of 50 to 60 petals.
3. Rich apricot flower color.
4. Continuous repeat flowering after the second year of planting.
5. Plants can be grown on their own roots; grafting is not required.
6. Dark glossy foliage is resistant to black spot and powdery mildew diseases.

PARENT COMPARISON

Plants of the new cultivar 'ALTenglanda' are similar to plants of the seed parent, in most horticultural characteristics, however, plants of the new cultivar 'ALTenglanda' differ in the following:

1. Flowers of the new cultivar are rich apricot, while flowers of the seed parent are soft pink.

Plants of the new cultivar 'ALTenglanda' are similar to plants of the pollen parent in most horticultural characteristics, however, plants of the new cultivar 'ALTenglanda' differs in the following;

1. The new cultivar has an upright climbing habit, while the pollen parent has an upright shrub habit.
2. Flowers of the new cultivar have 50 to 60 petals; flowers of the pollen parent have around 25 petals.

COMMERCIAL COMPARISON

Plants of the new cultivar 'ALTenglanda' can be compared to the commercial variety *Rosa* 'Brandy', unpatented. These varieties are similar in most horticultural characteristics, however 'ALTenglanda' differs in the following:

1. The new cultivar produces about 50 to 60 petals, while this comparator produces about 25 petals.
2. Plants of the new cultivar do not need to be grafted to grow vigorously; plants of this comparator require grafting for adequate vigor.

Plants of the new cultivar 'ALTenglanda' can also be compared to the commercial variety *Rosa* 'Edith's Darling', unpatented. These varieties are similar in most horticultural characteristics, however 'ALTenglanda' differs in the following:

1. Flowers of the new cultivar are around 12 cm in diameter; flowers of this comparator are around 8 cm in diameter.
2. Flower color of the new variety is a darker apricot than the flower color of this comparator.
3. Plants of the new cultivar do not need to be grafted to grow vigorously; plants of this comparator require grafting for adequate vigor.

BRIEF DESCRIPTION OF THE PHOTOGRAPH

The accompanying photograph illustrates in full color a close-up of an individual flower. The photograph was taken using conventional techniques and although colors may appear different from actual colors due to light reflectance it is as accurate as possible by conventional photographic techniques

DETAILED BOTANICAL DESCRIPTION

In the following description, color references are made to The Royal Horticultural Society Colour Chart 2015 except where general terms of ordinary dictionary significance are used. The following observations and measurements describe 'ALTenglanda' plants grown outdoors, in Vista, California. The growing temperature ranged from approximately 10° C. to 38° C. during the day and from approximately 5° C. to 22° C. during the night. Measurements were taken in September. General light conditions were very bright, normal sunlight. Measurements and numerical values represent averages of typical plant types.

Botanical classification: *Rosa* 'ALTenglanda'.

Market classification: Climbing rose.

PROPAGATION

Time to initiate roots: About 15 days at approximately 20° C.

Time to produce a rooted cutting: About 35 days at approximately 20° C.

PLANT

Age of plant described: Approximately 1.5 years.

Growth habit: Semi-upright, outwardly spreading.

Container size: 2-gallon.

Height: 60 cm.

Plant spread: 35 cm.

Rootstock: Own root.

Growth rate: Rapid.

Branching characteristics: Sympodial branching.

Length of primary lateral branches: Average range 18 to 34 cm.

Diameter of lateral branches: Approximately 4 to 6 mm.

Quantity of branches: 4 to 5 main branches, moderate lateral branches, 4 to 8 lateral branches per main branch.

Branches — young wood:

*Diameter.*—Approximately 6 mm.

*Texture.*—Glabrous.

*Approximate density/quantity of prickles.*—Moderate.

*Color.*—Near RHS Green 137D.

Branches — old wood:

*Diameter.*—Approximately 8 to 16 mm.

*Color.*—Near RHS Green 137B streaked Greyed-Green 195A.

*Texture.*—Glabrous. Oldest, basal growth scaly.

Thorns:

*Approximate density/quantity of thorns.*—Young growth: Moderate. 1 cm long, base 4 mm in diameter. Moderately hooked Colored near Yellow-Green 151D, strongly flushed Greyed-Red 182A and 182B, especially at base. Mature growth: Moderate. Approximately 4 mm in diameter at base. 5 mm long. Colored near RHS Greyed-Orange 165C, flushed 165B.

FOLIAGE

Leaf:

*Arrangement.*—Alternate and compound.

*Quantity.*—Average 5 to 10 per main branch.

*Internode.*—Average range 2.2 to 2.7 cm.

*Average length.*—Approximately 10 cm.

*Average width.*—Approximately 6 cm.

Rachis:

*Average length.*—Approximately 4.8 cm.

*Average diameter.*—Approximately 2 mm.

*Color.*—Upper surface: Near RHS Green 137C. Lower surface: Near RHS Green 143C.

*Texture.*—Glabrous. No prickles.

Leaflet (descriptors for lateral and terminal):

*Quantity.*—7 per leaf.

*Average length.*—Approximately 3.5 cm to 4 cm.

*Average width.*—Approximately 2.5 cm.

*Shape of blade.*—Broad ovate.

*Apex.*—Acute.

*Base.*—Broadly rounded.

*Margin.*—Finely serrate.

*Margin undulation.*—Weak.

*Appearance of top surface.*—Moderately glossy.

*Appearance of bottom surface.*—Matte.

*Texture of top surface.*—Glabrous.

*Texture of bottom surface.*—Glabrous.

*Color.*—Young foliage upper side: Near RHS Yellow-Green 145A. Veins Green 137A. Marginal flush Greyed-Purple 185A on emerging foliage. Young foliage under side: Near RHS Yellow-Green 147D. Veins 137C. Emerging foliage flushed Greyed- Purple 185B. Mature foliage upper side: Near RHS Green NN137A. Mature foliage under side: Near RHS Green 137D.

*Venation*.—Type: Reticulate. Venation color upper side: Near RHS Green 137C. Venation color under side: Near RHS Yellow-Green 145A.

Petiole:

*Average length*.—Approximately 2 cm.

*Average diameter*.—Approximately 3 mm.

*Texture*.—Glabrous.

*Color*.—Upper surface: Near RHS Green 137D. Lower surface: Near RHS Green 143B.

*Petiole wing*.—Typically 15 mm long and 6 mm wide. Apex apiculate. Upper surface colored near RHS Green 137D, lower surface colored near Green 143A. Texture: Glabrous.

FLOWER

Natural flowering season: Spring until Autumn.

Inflorescence type and habit: Fully double rotate flowers. Dense petals.

Flowers per inflorescence: 2 to 6.

Rate of flower opening: Approximately 5 days from bud to fully opened flower.

Flower longevity on plant: About 7 days after fully opened.

Quantity of flowers: 30 to 40 fully opened flowers and buds per plant in full bloom.

Flower size:

*Diameter*.—Approximately 12 cm.

*Height*.—Approximately 8 cm.

Flower shape:

*From above*.—Round to very slightly irregular round.

*Profile of upper part of flower*.—Flattened convex to nearly convex with maturity.

*Profile of lower part of flower*.—Flattened convex, lower petals reflexing significantly with age. Petals reflex one by one.

Peduncle:

*Length*.—4.5 cm.

*Diameter*.—4 mm.

*Color*.—Near RHS Green 143B.

*Texture*.—Densely covered in very small, not sharp prickles. Prickles about 3 mm long and colored near Greyed-Orange 173D.

Pedicel:

*Length*.—3 to 5 cm.

*Diameter*.—4 mm.

*Color*.—Near RHS Green 143B.

*Texture*.—Densely covered in very small, not sharp prickles. Prickles about 2 mm long and colored near Greyed-Orange 173D.

Petals:

*Petal arrangement*.—Multiple rotate, overlapping whorls.

*Petal quantity*.—Average 50 to 60.

*Length*.—4 to 6 cm.

*Width*.—2.3 to 4.7 cm.

*Shape*.—Broad deltate.

*Margin*.—Entire. Moderately ruffled

*Apex*.—Rounded with 2 to 5 irregular shallow notches.

*Base*.—Very broad attenuate.

*Texture*.—Glabrous all surfaces.

*Color*.—When opening: Upper surface: Near RHS Yellow-Orange 16D, flushed Orange 29B. Base strongly flushed Yellow 6A in a small basal spot. Lower surface: Near RHS Yellow-Orange 16D, flushed Orange 29B. Base strongly flushed Yellow 10A. Fully opened: Upper surface: Near RHS Orange 29D. Base strongly flushed Yellow 10A in a small basal spot. Lower surface: Near RHS Orange 29D. Base strongly flushed Yellow 10A. Aging: Upper surface: Near RHS Yellow 11D, lightly flushed 29D. Basal blotch 10B. Lower surface: Near RHS Yellow 11D, lightly flushed 29D. Basal blotch 10B in a small basal spot.

Bud:

*Shape*.—Ovate.

*Length*.—Approximately 3 cm.

*Diameter*.—Approximately 2 cm.

*Color*.—Near RHS Yellow-Orange 15D. Lightly flushed Orange-Red 33C.

Sepals:

*Quantity*.—5.

*Length*.—3 cm.

*Width*.—15 mm.

*Shape*.—Narrow deltoid.

*Apex*.—Apiculate. Weak sepal extensions.

*Margin*.—Entire.

*Texture*.—Slightly pubescent lower surface, densely and softly pubescent upper surface.

*Color*.—Interior Surface: Near RHS Green 138C. Exterior Surface: Near RHS Green 137A.

Receptacle:

*Depth*.—5 mm.

*Diameter*.—8 mm.

*Shape*.—Flat.

*Color*.—Near RHS Yellow-Green 145D.

Fragrance: Moderate lemony tea rose scent.

REPRODUCTIVE ORGANS

Stamens:

*Quantity*.—About 60.

*Filament length*.—5 mm to 8 mm.

*Filament color*.—Near RHS White 155D.

Anthers:

*Length*.—2 mm.

*Shape*.—Oblate.

*Color*.—Near RHS Greyed-Orange166A.

*Pollen*.—None observed.

Pistil: Misshapen 3-parted structure in center of receptacle. About 5 mm in length and 4 mm in diameter. Colored near RHS Greyed-Yellow 161A.

OTHER CHARACTERISTICS

Seeds and fruits: Not observed.

Disease/pest resistance: Very good resistance to blackspot (*Diplocarpon rosae*) and powdery mildew (*Podosphaera pannosa*) disease observed. Neither resistance nor susceptibility to other normal diseases and pests of roses observed.

What is claimed is:

1. A new and distinct cultivar of Rose plant named 'ALTenglanda' as herein illustrated and described.

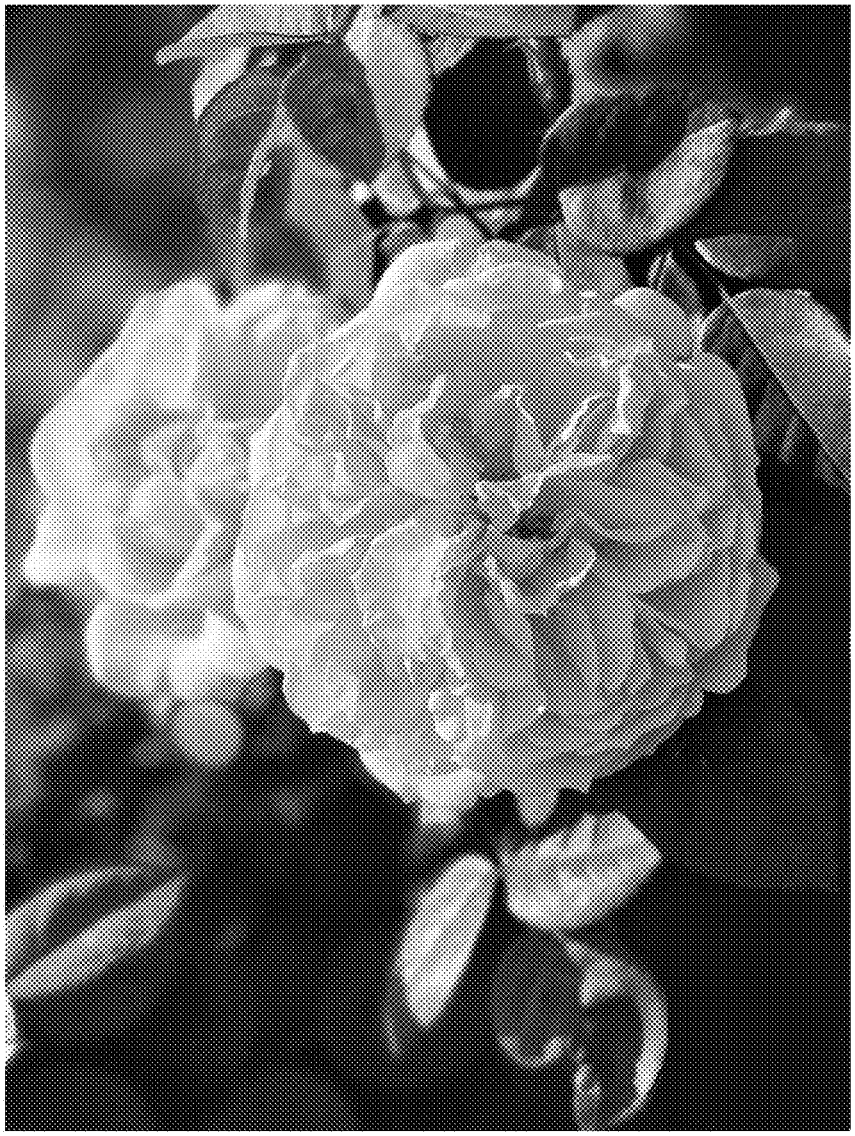

* * * * *